United States Patent
Senegas et al.

(10) Patent No.: US 9,523,750 B2
(45) Date of Patent: Dec. 20, 2016

(54) DETERMINATION OF A MAGNETIC RESONANCE IMAGING PULSE SEQUENCE PROTOCOL CLASSIFICATION

(75) Inventors: Julien Senegas, Hamburg (DE); Stefanie Remmele, Hamburg (DE); Michael Lee, Arlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 630 days.

(21) Appl. No.: 14/002,206

(22) PCT Filed: Feb. 21, 2012

(86) PCT No.: PCT/IB2012/050782
§ 371 (c)(1),
(2), (4) Date: Aug. 29, 2013

(87) PCT Pub. No.: WO2012/117314
PCT Pub. Date: Sep. 7, 2012

(65) Prior Publication Data
US 2013/0338930 A1 Dec. 19, 2013

(30) Foreign Application Priority Data
Mar. 1, 2011 (EP) .................................... 11156420

(51) Int. Cl.
*G01R 33/54* (2006.01)
*G01R 33/56* (2006.01)
(Continued)

(52) U.S. Cl.
CPC ............. *G01R 33/54* (2013.01); *G01R 33/543* (2013.01); *G01R 33/546* (2013.01);
(Continued)

(58) Field of Classification Search
CPC ..... G01R 33/54; G01R 33/546; G01R 33/543; G01R 33/5608; G06F 19/34; G06F 19/6406; G06F 19/321; G06F 11/327
See application file for complete search history.

(56) References Cited

U.S. PATENT DOCUMENTS 6,687,527 B1 * 2/2004 Wu ....................... G01R 33/546
324/318
7,051,286 B1   5/2006 Stemmer
(Continued)

FOREIGN PATENT DOCUMENTS

EP          1061376 A2      12/2000
JP     2008200071 A  *  9/2008
(Continued)

OTHER PUBLICATIONS

Simmons, Andrew et al "The AddMeuroMed Framework for Multi-centre MRI Assessment of Alzheimer's Disease: Experience from the First 24 Months", International Journal of Geriatric Psychiatry, vol. 26, No. 1, Apr. 2010.
(Continued)

*Primary Examiner* — David Gray
*Assistant Examiner* — Laura Roth

(57) ABSTRACT

A medical imaging device (300) includes a magnetic resonance imaging system (302) and a memory (334) containing machine executable instructions (370, 372, 374, 376, 378, 380, 382, 384, 386) for execution by a processor (328). Execution of the instructions causes the processor to receive (100, 204) a pulse sequence protocol (340). Execution of the instructions further causes the processor to determine (102, 206) a pulse sequence type classification (342) descriptive of the pulse sequence protocol. Execution of the instructions further cause the processor to determine (104, 208) a magnetic resonance contrast classification (344). The choice of the magnetic resonance contrast classification depends upon the pulse sequence type classification. Execution of the instructions further causes the processor to determine (106,
(Continued)

210) a pulse sequence protocol classification (346). The pulse sequence protocol classification is determined by the pulse sequence type classification and the magnetic resonance contrast classification.

20 Claims, 5 Drawing Sheets

(51) Int. Cl.
  G06F 19/00 (2011.01)
  G06F 11/32 (2006.01)
(52) U.S. Cl.
  CPC ....... *G01R 33/5608* (2013.01); *G06F 19/321* (2013.01); *G06F 19/34* (2013.01); *G06F 19/3406* (2013.01); *G06F 11/327* (2013.01)

(56) References Cited

U.S. PATENT DOCUMENTS

2009/0091324 A1* 4/2009 Sugiura .............. G01R 33/4828
                                                          324/309

2010/0052680 A1   3/2010  Wohlfarth
2010/0092056 A1   4/2010  Rofsky
2010/0198373 A1   8/2010  Krellmann

FOREIGN PATENT DOCUMENTS

JP    2009101133 A    5/2009
JP    2009153965 A    7/2009
WO    03021284 A1     3/2003

OTHER PUBLICATIONS

Brennan, Darren D. et al "Rapid Automated Measurement of Body Fat Distribution from Whole-Body MRI", American Journal of Roentgenology, vol. 185, No. 2, Aug. 2005, pp. 418-423.

McAuliffe, M.J. et al "Medical Image Processing Analysis and Visualization in Clinical Research", Proceedings 14th IEEE Symposium on Computer-Based Medical Systems. Jul. 2001, pp. 381-386.

Jiang, Chunyan et al "Segmentation and Quantification of Brain Tumor", Virtual Environments, Human-Computer Interfaces and Measurement System S. 2004, pp. 61-66.

* cited by examiner

DETERMINATION OF A MAGNETIC RESONANCE IMAGING PULSE SEQUENCE PROTOCOL CLASSIFICATION

CROSS-REFERENCE TO PRIOR APPLICATIONS

This application is the U.S. National Phase application under 35 U.S.C. §371 of International Application No. PCT/IB2012/050782, filed on Feb. 21, 2012, which claims the benefit of European Patent Application No. 11156420.9, filed on Mar. 1, 2011. These applications are hereby incorporated by reference herein.

TECHNICAL FIELD

The invention relates to magnetic resonance imaging, in particular to the classification of pulse sequence protocols.

BACKGROUND OF THE INVENTION

Magnetic resonance (MR) parameters define the image acquisition that is performed on the scanner and consequently define the types of image (contrasts) that are generated. These parameters may be pre-defined at a radiology department as pulse sequence protocols. These protocols may further be modified by technicians for a specific patient; alternatively, the parameters may be set independently for new patients. Setting-up MR protocol parameters to achieve a desired contrast type requires expert knowledge of MR physics. Recommendations from MR literature and vendors' user guides or user forums are useful information sources, but are rarely consulted in daily practice due to lack of time. Hence, it can happen that subtle changes in the parameters have an undesired influence on the resulting image contrast.

Analysis based on field data shows that not only geometry parameters are routinely adapted by the technician, but also parameters having an influence on image quality, scan time, or contrast. The degree to which scan parameters are optimized by the user greatly varies within institutions or technicians. Examples of user interface parameters requiring more or less frequent adaptation by the technician include: field of view, resolution, number of slices, slice gap, fold over direction, parallel imaging mode, parallel imaging acceleration factor, number of averages, echo time, repetition time.

SUMMARY OF THE INVENTION

The invention provides for a medical imaging device, a computer program product, and a method.

Currently, the definition of Magnetic Resonance (MR) pulse sequence protocols is done from a technical point of view, by specifying the value of a large list of scan parameters.

However, this definition of the protocol is not done using the context of the desired clinical use, i.e. the desired image contrast type. Hence, expert knowledge is required to predict the contrast resulting from a particular choice of parameter setting or to avoid unwanted contrast alteration when adapting scan parameters. This has two disadvantages:

A lack of operator guidance in design mode of pulse sequence protocols, when setting up a new protocol An absence of control of contrast fidelity when the operator modifies certain protocol parameters.

Embodiments of the invention may address a solution to these and other disadvantages.

In some cases, the operator is not aware that a parameter change can have a strong influence on the resulting contrast. For example, when repetition time (TR) is set to "shortest" in a multi-slice spin-echo scan, increasing or decreasing the number of slices can have a very strong impact on the TR value. The resulting contrast can vary from T1 weighted (T1W), proton density weighted (PDW), and T2 weighted (T2W).

The invention may solve these and other problems by computing and indicating the contrast type associated with the current value of protocol parameters and displaying a warning message when the initial contrast class is modified.

Embodiments of the invention may perform the following steps: (1) obtain the current pulse sequence parameters from the MR system; (2) apply a classification engine to these parameters to define the current scan as belonging to a specific contrast class; (3) repeat actions 1-2 as the user of the invention modifies the scan parameters; (4) notify the user when the contrast class found in step 2 differs from the original class.

The invention uses a rule-based mechanism to define contrast specific MR protocol classes such as T1 weighted Spin Echo (T1W-SE), Proton Density Weighted Spin Echo (PDW-SE), T2 Weighted Turbo Spin Echo (T2W-TSE), T2 weighted Fluid Attenuation Inversion Recovery (T2W-FLAIR), T1 Weighted Inversion Recovery Turbo Spin Echo (T1W-IR-TSE), and etc. This classification is based on the value of protocol parameters and indications given in the MR literature. Hence, when the operator sets-up or modifies a protocol, the corresponding protocol class is displayed for information and the operator can be notified if the performed protocol changes run the risk to alter the contrast. The ontology used to describe the protocol classes should be based on common usage in the radiology community.

Embodiments of the invention may use a two-step classification method. First, an exhaustive partition of the parameter space is obtained by considering all possible value combinations of some key protocol parameters (imaging technique, scan mode, fast imaging mode, etc). Then, the classes obtained in the first step are refined by defining specific value ranges for the main MR contrast parameters such as echo-time, repetition time, inversion delay, flip angle, and etc.

The criteria used to define this rule-based classification can be taken from recommendations from the MR community (review papers) and from current clinically used pulse sequences.

This classification method is generic, but allows for application-specific rules to be implemented in the second step (e.g. for neuro, musculoskeletal—MSK, body/oncology). The granularity of the classification (number of different classes defined and degree of differentiation between the classes) can be adapted, e.g. by adjusting the number of key contrast parameters used in the first step (e.g. fat suppression).

Embodiments of the invention may comprise an MR protocol editing unit, a unit for classification, and a display unit. The MR protocol editing unit and the unit for classification may be computational devices. The display unit may be a user interface.

A unit for MR protocol editing can be the default protocol editor available on the MR console. Alternatively, this can be an off-line protocol editor, with the possibility to load, edit and save MR pulse sequence protocols for future usage. Normally, this unit is linked to another unit that checks for possible conflicts between parameters.

A unit for protocol classification takes as input the list of parameters defining a MR pulse sequence protocol, and returns as output a contrast class that best matches the values of the input protocol parameters. The contrast class may be referred to as a pulse sequence protocol classification.

At minimum, the protocol classification unit should be activated when a protocol is first loaded into the protocol editor (to determine the initial class). Thereafter, in some embodiments, this unit may be activated automatically upon making any parameter changes via the protocol editor unit. In an alternative embodiment, the unit may be activated upon a specified user interaction, such as when the user saves the protocol.

Embodiments of the invention may use a two-step classification method:
1. First, a number of generic classes, also referred to as a pulse sequence type classification, are defined based on the values of key protocol parameters, such as imaging technique (i.e., Inversion Recovery (IR), Spin Echo (SE), Fast Field echo (FFE)), scan mode (i.e., two-dimensional (2D), three-dimensional (3D), Multi Slice (MS), Multi Slice Two-Dimensional (M2D)), and fast imaging mode (i.e., Echo Planar Imaging (EPI), Turbo Spin Echo (TSE), Turbo Field Echo (TFE), Gradient Echo and Spin Echo (GRASE), and Turbo Field Echo and Echo Planar Imaging (TFEEPI)). Since these parameters all take only a limited number of well defined values, an exhaustive partition of the multi-dimensional protocol space can be achieved in this way.
2. Then, a second classification step refines the contrast classes, based on the definition of value ranges for contrast parameters such as echo time, repetition time, inversion delay, etc. The criteria used to define this rule-based classification can be taken, for example, from recommendations from the MR review papers. Note that contrast parameters and the threshold values used in this second step are not the same for all the generic classes obtained after the first step, but need to be specified case by case. For example, for the generic class SE, the following classes can be defined depending on echo time (TE) and TR solely:
a. PDW: 10<TE<25 ms, TR>1800 ms
b. weak T2W: 30<TE<70 ms, TR>1800 ms
c. T2W: TE>80 ms, TR>1800 ms
d. strong T2W: TE>200 ms, TR>1800 ms
e. weak T1W: TE<30 ms, 1000<TR<1800 ms
f. T1W: 10<TE<25 ms, 200<TR<700 ms
g. mixed T1T2W: TE>30 ms, TR<1500 ms Note that the second step may not partition exactly the protocol space, i.e. there may not exist a contrast class for some combinations of protocol parameters. This is also valuable information for the operator.

When applying this two-step classification, contrast-specific classes are obtained, such as T1W-SE, PDW-SE, T2W-TSE, T2W-FLAIR, T1W-IR-TSE, and etc.

This classification method is generic, but allows for application-specific rules to be implemented in the second step (e.g. for Neuro, MSK, body/onco). The granularity of the classification (number of different classes defined and degree of differentiation between the classes) can be adapted, e.g. by adjusting the number of key contrast parameters used in the first step (e.g., fat suppression).

Note that these two steps may not be necessary performed successively, but alternatively in several sub-steps. For example, one may first use some key parameters such as imaging technique to define the first partition, then apply the class refinement based on echo time and repetition time values, and finally refine the obtained classes according to other key parameters such as scan mode, fat suppression.

In other words, the order in which the rules are applied may not be fixed, but the resulting combination of rules is important.

Note that this rule-based classification can be implemented using Boolean operators (AND, OR, etc) and "if" statements as a computer program. In other alternative embodiments, mathematical operations of arbitrary complexity are used to compute functions based on a plurality of parameters; the result of this computation may then be subject to rules defining the contrast class.

It is also proposed to store the computed pulse sequence protocol class as dedicated image parameter in the proprietary image formats and/or in the DICOM format (e.g. as DICOM tag) and to show the value of the protocol class in the info box when displaying the acquired images, along protocol name, TE, and TR for example. This would facilitate reading of the images by the radiologist and could be useful when retrieving the images from a Picture Archiving and Communication System (PACS).

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

An 'image segmentation module' or 'segmentation module' as used herein encompasses computer executable code that is adapted for automatically identifying anatomical structures in an image or within image data. A segmentation module may for instance be, but is not limited to: a pattern recognition module, a trained pattern recognition module, an edge recognition algorithm, or a model adapted for fitting a deformable model to image data, or a feature identification algorithm.

The edges in a two-dimensional or three-dimensional volume may be detected with an edge detection module. This can be accomplished with a suitable edge detection algorithm such as the Sobel operator. Other alternatives include algorithms based upon: the Canny edge detector, the differential edge detector, the Marr-Hildreth operator, the phase congruency based edge detector, the Laplace operator, the Deriche edge detector, the Rothwell edge detector, the Prewitt operator, the Kirsch operator, the Hueckel operator, and the Roberts operator. The Sobel operator operates in specific planes of the three-dimensional volume. The Sobel operator can be applied to voxels that all lie in the same plane. The Sobel operator can also be applied to planes that do not lie within a plane of voxels. In this case, the voxels are weighted by according to how much of the voxel is intersected by the plane.

Anatomical landmarks may be identified using an anatomical landmark module using the set of edges. The three-dimensional volume is the segmented using a first shape constrained deformable model using a first segmentation module. A shape constrained deformable model is a three dimensional model of the patient's anatomy, which is deformed by the segmentation module to fit feature points. As the shape constrained deformable model is iteratively deformed to fit feature points, which are calculated using both the model and image data. Feature points can be extracted from an image using a feature detection algorithm. The model calculates the stress and strain on the surface of the model as well as the internal forces caused by the deformation.

A trained pattern recognition module is a pattern recognition module can be trained using a set of training images, where the volume or volumes of interest have been correctly placed. This could be implemented using a variety of different methods. Examples of different methods or algorithms that could be used are: Principal Component Analysis, Neural Network, CN2 algorithm, C4.5 algorithm, Iterative Dichotomiser 3 (ID3), Nearest neighbor search algorithm, naive Bayes classifier algorithm, Holographic Associative Memory, or perception learning algorithm.

A feature identification algorithm can be an algorithm such as the Hough Transform or the Scale-Invariant Feature Transform (SIFT). These algorithms have the advantage of being able to identify complex geometry. The feature identification algorithm can also be a custom algorithm which is based upon prior knowledge of the anatomy. For instance the diaphragm is easily identifiable in a MRI image. An edge detection algorithm will locate the border of the diaphragm, and a connected component analysis will produce a surface which can be identified and used by the first segmentation module.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'computing device' as used herein encompasses to any device comprising a processor. A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses a interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

A 'database' as used herein encompasses a data file or repository which contains data that may be accessed by a processor. Examples of databases are, but are not limited to: a data file, a relational database, a file system folder containing data files, and a spreadsheet file.

In one aspect the invention provides for a medical imaging device comprising a magnetic resonance imaging system for acquiring magnetic resonance data from a subject. The medical imaging device further comprises a processor for controlling the medical image device. For instance the processor may control the function and operation of the magnetic resonance imaging system. The medical imaging device further comprises a memory containing machine executable instructions for execution by the processor. Execution of the machine executable instructions causes the processor to receive a pulse sequence protocol. The pulse sequence protocol comprises instructions which cause the magnetic resonance imaging system to acquire the magnetic resonance data. For instance the pulse sequence protocol may contain instructions which cause the magnetic resonance imaging system to perform various operations at specific times relative to each other. A pulse sequence protocol is often referred to as simply a pulse sequence.

Execution of the machine executable instructions further cause the processor to determine a pulse sequence type classification descriptive of the pulse sequence. A pulse sequence type classification may be considered a generic classification of the pulse sequence protocol. For instance the pulse sequence type classification may be based on the imaging technique, the scan mode, and/or the fast imaging mode. It is advantageous to begin to classify the pulse sequence protocol in this way because parameters on which the pulse sequence type classification is based have a limited number of discrete values. This provides an efficient way to divide the multidimensional parameter space that defines a pulse sequence protocol into groups of pulse sequence protocols.

Execution of the machine executable instructions causes the processor to determine a magnetic resonance contrast classification. The choice of a magnetic resonance contrast classification is dependent upon the pulse sequence type classification. In other words the magnetic resonance contrast classification is determined or selected in accordance with the pulse sequence type classification. A magnetic resonance contrast classification is based on the value ranges of parameters which affect the contrast of the magnetic resonance image. Very often the parameters used to determine the magnetic resonance contrast classification are continuous in value as opposed to being discrete. For instance they may be, but are not limited to: the echo time, repetition time, inversion delay, flip angle, and other such parameters. Execution of the instructions further causes the processor to determine a pulse sequence protocol classification. The pulse sequence protocol classification is determined by the pulse sequence type classification and the magnetic resonance contrast classification. In some embodiments the pulse sequence protocol classification is also determined by elements or values stored in the pulse sequence protocol.

This embodiment may be advantageous because when a pulse sequence protocol is so classified the images derived from the magnetic resonance data acquired using the pulse sequence protocol will have similar image and contrast characteristics and may thus be compared and analyzed. For instance magnetic resonance data which contains anatomical data describing tumors within a subject may be segmented and compared when the pulse sequences used to acquire them have the same pulse sequence protocol classification.

In another embodiment execution of the machine executable instructions further cause the processor to receive a selected pulse sequence protocol with an initial pulse sequence protocol classification. Execution of the instructions further causes the processor to receive modifications to the selected pulse sequence protocol. The modified selected pulse sequence protocol is received as the pulse sequence protocol. This embodiment is advantageous because a standard pulse sequence protocol can be retrieved from a database. An operator may then modify the selected pulse sequence protocol and then it is re-classified. This is advantageous because then an operator may know if the pulse sequence protocol still has the same pulse sequence protocol classification or not. This may be useful in a clinical situation where multiple operators are using a system and it is desirable to compare the results prepared by the different operators. It may also be useful for comparing magnetic resonance data or images derived there from which were acquired at different clinical facilities. The method provides an efficient and objective way of classifying pulse sequence protocols.

In another embodiment execution of the instructions further causes the processor to display a warning message on a display if the pulse sequence protocol classification is not identical with the initial pulse sequence protocol classification. This embodiment is advantageous because an operator is explicitly warned that the pulse sequence protocol classification is not identical with the initial pulse sequence protocol classification. This may reduce the chance that the operator acquires magnetic resonance data which may not be used later to compare to other or previously acquired magnetic resonance data.

In another embodiment execution of the machine executable instructions further cause the processor to determine corrective modifications to the pulse sequence protocol if the pulse sequence protocol classification is not identical with the initial pulse sequence protocol classification. The corrective modifications are descriptive of further modifications to the pulse sequence protocol which will return it to the initial pulse sequence protocol classification. Execution of the instructions further causes the processor to display a correction message on a display. The correction message is descriptive of the corrective modifications. For instance the instructions may contain a software module which examines the values or parameters of the pulse sequence protocol and determines which ones need to be changed such that the pulse sequence protocol will then have a pulse sequence protocol classification which matches or is identical to the initial pulse sequence protocol classification. Displaying the corrective message may be beneficial because then the operator will be able to enter values into a user interface or graphical user interface which modify the pulse sequence protocol such that it then has a pulse sequence protocol classification which is equal to the initial pulse sequence protocol classification.

In another embodiment execution of the machine executable instructions further causes the processor to display the initial pulse sequence protocol on a graphical user interface such that the manipulation of the graphical user interface with a human interface device allows modification of the initial pulse sequence protocol. The modifications are at least partially received from the human interface device. Execution of the instructions further causes the processor to display allowed modifications on the graphical user interface. The allowed modifications are descriptive of the modifications which will make the pulse sequence protocol classification identical with the initial pulse sequence protocol classification. This embodiment may be beneficial because the allowed modifications allow an operator to see which values he or she may select to modify the pulse sequence protocol and allow it to still contain the same pulse sequence protocol classification.

In another embodiment execution of the instructions further causes the processor to acquire the magnetic resonance data using the magnetic resonance imaging system in accordance with the pulse sequence protocol. In other words the pulse sequence protocol is used to generate commands which the processor can use to acquire the magnetic resonance data. For instance a software module may interpret the pulse sequence protocol and then generate commands which the processor can send to the magnetic resonance imaging system. These commands then cause the magnetic resonance imaging system to acquire the magnetic resonance data. Execution of the machine executable instructions further cause the processor to reconstruct a magnetic resonance image from the magnetic resonance data.

In another embodiment execution of the machine executable instructions further cause the processor to append a pulse sequence protocol classification tag to the magnetic resonance image. The pulse sequence protocol classification tag may comprise data or meta-data which identifies the pulse sequence protocol used to acquire the magnetic resonance data which was used to reconstruct the magnetic resonance image.

For instance the magnetic resonance image may be stored in a format which includes Meta data describing the magnetic resonance image. For instance the image may be stored in the DICOM format. The DICOM format may have a DICOM tag. Appending a pulse sequence protocol classification tag to the magnetic resonance image may be advantageous because it facilitates the comparison of the magnetic resonance image with other magnetic resonance images. For instance images all acquired from the same patient may then be compared to track the progress of a disease or the healing of an injury. The pulse sequence protocol classification tag may be used to ensure that images with the same contrast are only compared. Images from different people may be used to compare different types of the same anatomical structure in similar images. For instance this may facilitate the use of diverse magnetic resonance images for training pattern recognition modules and/or deformable models for the identification of anatomical structures.

In another embodiment execution of the machine executable instructions further cause the processor to determine a set of magnetic resonance images. The set of magnetic resonance images each have a pulse sequence protocol tag identical with the pulse sequence protocol tag. For instance a collection of magnetic resonance images may be stored in a database or within a file system. The file system or database may be searched and those images which have a pulse sequence protocol classification that is identical with the pulse sequence protocol classification are grouped into the set. This for instance may be beneficial when images for a particular patient are to be compared. In this way images which have the same contrast characteristics can be automatically selected. When comparing images from different subjects images which have similar contrast classifications may also be grouped together into a set. This may be used for the process of training a system which automatically locates or segments anatomical structures in an image.

In another embodiment execution of the instructions further causes the processor to segment the magnetic resonance image and the set of magnetic resonance images. This embodiment may be useful for comparing images from a particular subject to aid in a diagnosis or to track the progress of a disease. It may also be useful for training an image process system. The medical imaging device may comprise a software module which is able to automatically segment images. This for instance may be performed by methods that are standard and known in the art. For instance models which look for specific image features such as the diaphragm or there may be a software module which fits a deformable model to anatomical structures.

In another embodiment execution of the machine executable instructions further cause the processor to compare an anatomical structure in the segmented magnetic resonance image and the segmented set of magnetic resonance images. For instance the size of a tumor may be compared. In other embodiments the size of a lesion may be compared. In yet still other aspects a comparison between an anatomical structure may in multiple images be used for training purposes for training a software module for performing the segmentation.

In another embodiment execution of the instructions further cause the processor to access an image database containing magnetic resonance images. The image database may be a database containing magnetic resonance images or it may be a file system containing magnetic resonance images. Execution of the instructions further causes the processor to calculate a class-specific parameter statistic descriptive of the database. The class is defined by any one of the following: a pulse sequence type classification, a magnetic resonance contrast classification, a pulse sequence protocol classification, and combinations thereof. The parameter is an image feature descriptive of the magnetic resonance images. For instance the image feature may be a grey value intensity or a mathematical transform of a grey value intensity. The image feature may also be an image feature descriptive of an anatomical region identified within the image. This embodiment may be useful in image processing to train image modules for specific magnetic resonance imaging sequences.

In another embodiment execution of the machine executable instructions further cause the processor to access a pulse sequence database containing pulse sequence protocol parameters. Execution of the machine executable instructions further cause the processor to calculate a pulse sequence protocol parameter statistic for the database. The pulse sequence protocol parameter statistic is computed by selecting pulse sequence protocols having the same class, where the class is any one of the following: a pulse sequence type classification, a magnetic resonance contrast classification, a pulse sequence protocol classification, and combinations thereof. This embodiment may be useful for computing statistics about used pulse sequences and making recommendations for pulse sequence protocols to use for various imaging purposes.

In another embodiment the pulse sequence type classification is descriptive of the scan type. For instance the scan type may be a spectroscopic data or it may be an imaging type scan. The scan type may also specify images acquired for specific purposes, for example, but not limited to: T1, T2, T2-star or diffusion information.

In another embodiment the pulse sequence type classification is descriptive of the imaging sequence. For instance the imaging sequence may be, but is not limited to: a spin echo, inversion recovery, gradient echo, variations of the gradient echo, steady-state free precession, balance sequences, and other known image sequences.

In another embodiment the pulse sequence type classification is descriptive of the scan mode. Examples of the scan mode may be, but are not limited to: two-dimensional, three-dimensional, multi-slice, one-dimensional, and multiple two-dimensional images or slices.

In another embodiment the pulse sequence type classification is descriptive of the fast imaging mode. The fast imaging mode may be for example, but is not limited to: fast spin echo, ultra-fast gradient echo, echo planar imaging, and other fast imaging techniques.

In another embodiment the pulse sequence type classification is descriptive of the shot mode. For instance the shot mode may be, but is not limited to: the multi-shot and single-shot.

In another embodiment the pulse sequence type classification is descriptive of the diffusion mode.

In another embodiment the pulse sequence type classification is descriptive of the dynamic mode.

In another embodiment the pulse sequence type classification is descriptive of the phase contrast mode.

In another embodiment the pulse sequence type classification is descriptive of the parallel imaging mode.

In another embodiment the pulse sequence type classification is descriptive of the fat suppression mode.

In another embodiment the pulse sequence type classification is descriptive of any combination of the aforementioned pulse sequence type classifications.

In another embodiment the magnetic resonance contrast classification is descriptive of the echo time.

In another embodiment the magnetic resonance contrast classification is descriptive of the repetition time.

In another embodiment the magnetic resonance contrast classification is descriptive of on the inversion delay.

In another embodiment the magnetic resonance contrast classification is descriptive of the flip angle.

In another embodiment the magnetic resonance contrast classification is descriptive of the diffusion B-value.

In another embodiment the magnetic resonance contrast classification is descriptive of the voxel size.

In another embodiment the magnetic resonance contrast classification is descriptive of any combination of the aforementioned magnetic resonance contrast classifications.

In another aspect the invention provides for a computing device comprising the processor, memory, and machine executable instructions of any of the aforementioned embodiments of the medical imaging device.

In another aspect the invention provides for a computer program product comprising machine executable instructions. For instance the machine executable instructions may be stored in a computer-readable storage medium. The medical imaging device comprises a magnetic resonance imaging system for acquiring magnetic resonance data from a subject. The medical imaging device further comprises a processor for controlling the magnetic resonance imaging system. Execution of the machine executable instructions causes the processor to receive a pulse sequence protocol. The pulse sequence protocol comprises instructions which cause the magnetic resonance imaging system to acquire the magnetic resonance data. Execution of the machine executable instructions further causes the processor to determine a pulse sequence type classification descriptive of the pulse sequence. Execution of the machine executable instructions further causes the processor to determine a magnetic resonance contrast classification. The choice of the magnetic resonance contrast classification is dependent upon the pulse sequence type classification. Execution of the machine executable instructions further causes the processor to determine a pulse sequence protocol classification. The pulse sequence protocol classification is determined by the pulse sequence type classification and the magnetic resonance contrast classification.

In another aspect the invention provides for a method of operating a medical imaging device. Likewise the method also provides for a computer-implemented method of operating a medical imaging device. The medical imaging device comprises a magnetic resonance imaging system for acquiring magnetic resonance data from a subject. The method comprises the step of receiving a pulse sequence protocol. The pulse sequence protocol comprises instructions which cause the magnetic resonance imaging system to acquire the magnetic resonance data. The method further comprises the step of determining a pulse sequence type classification descriptive of the pulse sequence. The method further comprises the step of determining a magnetic resonance contrast classification. The choice of the magnetic resonance contrast classification is dependent upon the pulse sequence type classification. The method further comprises the step of determining a pulse sequence protocol classification. The pulse sequence protocol classification is determined by the pulse sequence type classification and the magnetic resonance contrast classification.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
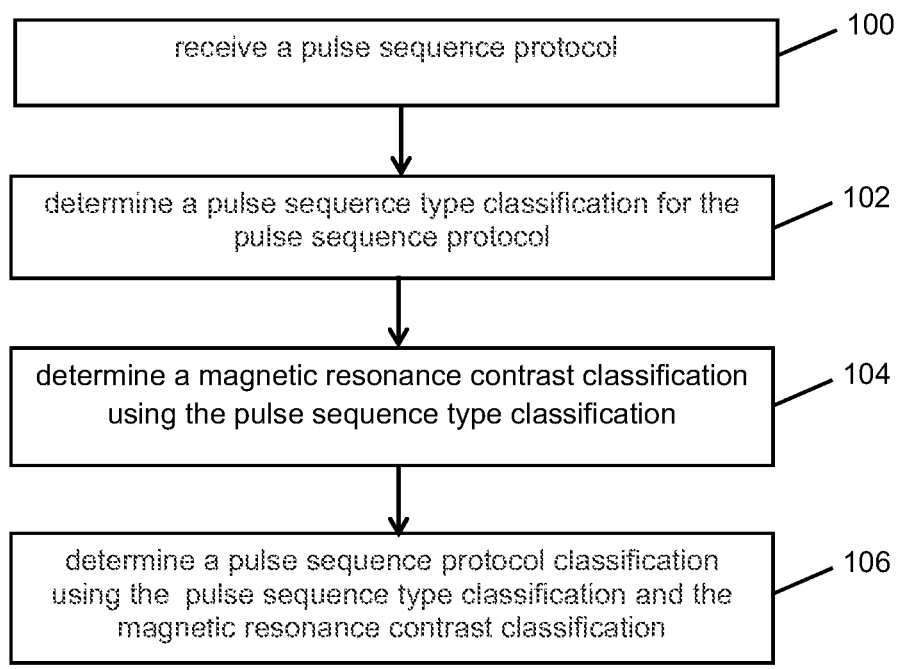
FIG. 1 shows a flow diagram which illustrates a method according to an embodiment of the invention.

FIG. 1 shows a flow diagram which illustrates a method according to an embodiment of the invention. In step 100 a pulse sequence protocol is received. In step 102 a pulse sequence type classification is determined for the pulse sequence protocol. Next in step 104 a magnetic resonance contrast classification is determined using the pulse sequence type classification. Finally in step 106 a pulse sequence protocol classification is determined using the pulse sequence type classification and the magnetic resonance contrast classification.

Figure 2:
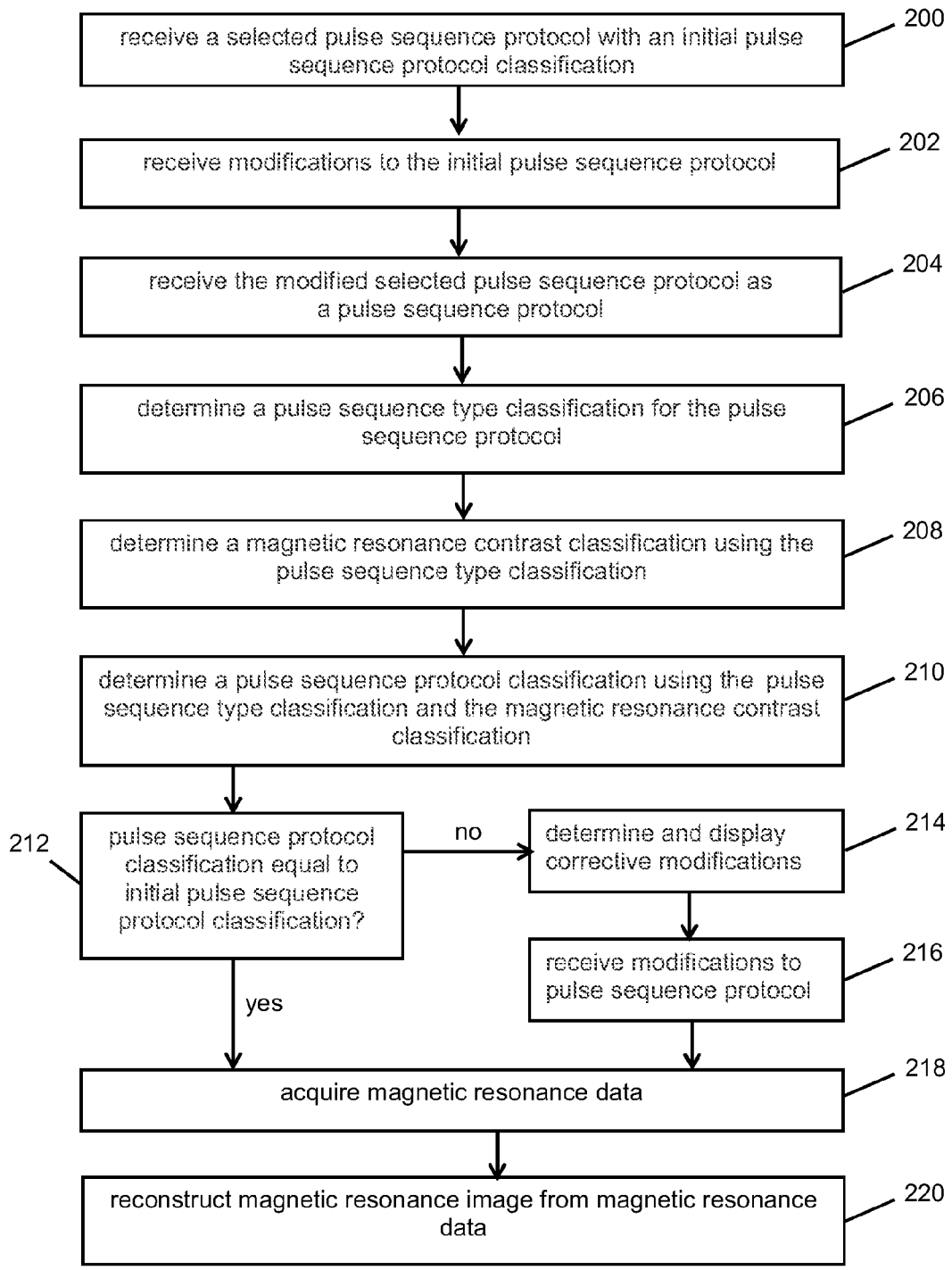
FIG. 2 shows a flow diagram which illustrates a method according to a further embodiment of the invention.

FIG. 2 shows a flow diagram which illustrates a method according to a further embodiment of the invention. In step 200 a selected pulse sequence protocol with an initial pulse sequence protocol classification is received. In step 202 modifications to the initial pulse sequence protocol are received. For instance they may be received in the form of a file or instructions containing modifications or the modifications may be received from a user interface such as a graphical user interface. Next in step 204 the modified selected pulse sequence protocol is received as a pulse sequence protocol. Next in step 206 a pulse sequence type classification is determined for the pulse sequence protocol. In step 208 a magnetic resonance contrast classification is determined using the pulse sequence type classification. In step 210 a pulse sequence protocol classification is determined using the pulse sequence type classification and the magnetic resonance contrast classification.

Next in step 212 the pulse sequence protocol classification is compared to the initial pulse sequence protocol classification. If the two are not identical then step 214 is performed. In step 214 corrective modifications which may be used to modify the pulse sequence protocol such that the pulse sequence protocol classification is equal to the initial pulse sequence protocol classification are determined. These corrective modifications are then also displayed on a display. Next in step 216 modifications to the pulse sequence protocol are received. In some instances the modifications may be a null set, that is to say that the operator decided to continue even though the pulse sequence protocol classification has changed. In other embodiments the corrective modifications do modify the pulse sequence protocol classification such that it is equal to the initial pulse sequence protocol classification.

Next in step 218 the magnetic resonance imaging system is used to acquire magnetic resonance data. Finally in step 220 the magnetic resonance image is reconstructed from the magnetic resonance data. Alternatively, if the pulse sequence protocol classification is equal to the initial pulse sequence protocol classification then from step 212 directly step 218 is performed. Again step 218 is the acquisition of magnetic resonance data. After the acquisition of magnetic resonance data a magnetic resonance image is reconstructed 220 from the magnetic resonance data.

Figure 3:
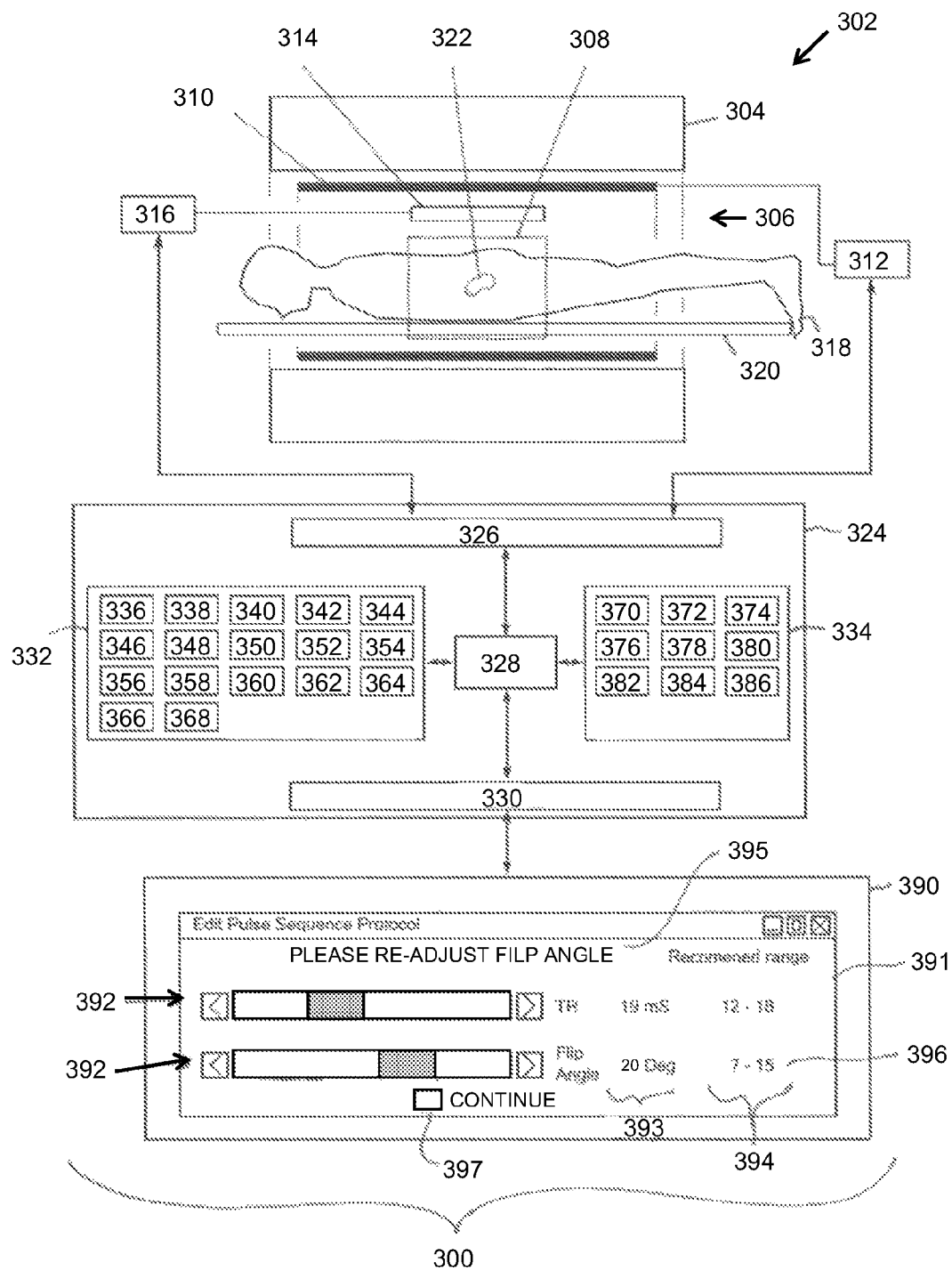
FIG. 3 illustrates a medical imaging device according to an embodiment of the invention.

FIG. 3 shows a functional diagram which illustrates a medical imaging device 300 according to an embodiment of the invention. The medical imaging device comprises a magnetic resonance imaging system 302. The magnetic resonance imaging system comprises a magnet 304. The magnet 304 is a cylindrical type superconducting magnet with a bore 306 through the center of it. The magnet shown in FIG. 3 is a cylindrical type superconducting magnet 304. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 306 of the cylindrical magnet 304 there is an imaging zone 308 where the magnetic field is strong and uniform enough to perform magnetic resonance imaging.

Also within the bore 306 of the magnet 304 is a set of magnetic field gradient coils 310. Within the bore of the magnet there is also a set of magnetic field gradient coils 310 which is used for acquisition of magnetic resonance data to spatially encode magnetic spins within an imaging zone 308 of the magnet 304. The magnetic field gradient coils 310 are connected to a magnetic field gradient coil power supply 312. The magnetic field gradient coils 310 are intended to be representative. Typically magnetic field gradient coils 310 contain three separate sets of coils for spatially encoding in three orthogonal spatial directions. The magnetic field gradient coil power supply 312 supplies current to the magnetic field gradient coils 310. The current supplied to the magnetic field gradient coils 310 is controlled as a function of time and may be ramped or pulsed.

Adjacent to the imaging zone is a radio-frequency coil 314 for manipulating the orientations of magnetic spins within the imaging zone 308 and for receiving radio transmissions from spins also within the imaging zone 308. The radio-frequency coil 314 may contain multiple coil elements. The radio-frequency coil 314 may also be referred to as a channel or an antenna. The radio-frequency coil 314 is connected to a radio frequency transceiver 316. The radio-frequency coil 314 and radio-frequency transceiver 316 may be replaced by separate transmit and receive coils and a separate transmitter and receiver. It is understood that the radio-frequency coil 314 and the radio-frequency transceiver 316 are simply representative. The radio-frequency coil is intended to also represent a dedicated transmit antenna and a dedicated receive antenna. Likewise the transceiver may also represent a separate transmitter and receivers.

A subject 318 is located partially within the imaging zone 308. The subject 318 is seen as reposing on a subject support 320. Within the subject 318 is an anatomical structure 322 which is located within the imaging zone 308.

The magnetic field gradient coil power supply 312 and the transceiver 316 are shown as being connected to a hardware interface 326 of a computer system 324. The computer system 324 further comprises a processor 328. The processor 328 is connected to the hardware interface 326. The processor 328 uses the hardware interface 326 to send and receive commands to the magnetic resonance imaging system 302. Via the hardware interface 326 the processor 328 is able to control the operation and function of the magnetic resonance imaging system 302. The processor 328 is shown as being further connected to a user interface 330, computer storage 332, and computer memory 334.

The computer storage 332 is shown as containing a selected pulse sequence protocol 336. The computer memory is also shown as containing an initial pulse sequence protocol classification 338 which is associated with and/or attached to the selected pulse sequence protocol 336. The computer storage 332 is further shown as containing a pulse sequence protocol 340. The pulse sequence protocol 340 is a modified version of the selected pulse sequence protocol 336. The computer storage 332 is also shown as containing a pulse sequence type classification 342 associated with or attached to the pulse sequence protocol 340. The computer storage 332 is further shown as containing a magnetic resonance contrast classification 344 for the pulse sequence protocol 340.

The computer storage 332 is further shown as containing a pulse sequence protocol classification 346 that is associated with and/or is attached to the pulse sequence protocol 340. The computer storage 332 is further shown as containing magnetic resonance data 348 that has been acquired using the magnetic resonance imaging system 302. The computer storage 332 is further shown as containing a magnetic resonance image 350 which has been reconstructed from the magnetic resonance data 348. The computer storage 332 is further shown as containing an image database 352. The image database 352 contains a plurality of magnetic resonance images. The computer storage 332 is further shown as containing a set of magnetic resonance images 354. They may for instance be magnetic resonance images which have identical pulse sequence protocol tags. The computer storage 332 is further shown as containing a set of image segmentations 356 for the set of magnetic resonance images 354.

The computer storage 332 is further shown as containing a comparison of anatomical structure or structures 358 for using the image segmentation 356 of the set of images 354. The computer storage 332 is further shown as containing a class-specific parameter statistic 360. The class-specific parameter statistic 360 is derived from the image database 352. The computer storage 332 is further shown as containing a pulse sequence database 362. The pulse sequence database 362 is a database for a file system containing pulse sequences or pulse sequence protocols. The computer storage 332 is further shown as containing a pulse sequence protocol classification tag. The pulse sequence protocol classification tag 364 is Meta data which is descriptive of the pulse sequence protocol classification of the magnetic resonance image 350. The pulse sequence protocol classification tag may be in some instances appended to the magnetic resonance image 350. The computer storage 332 is shown as further containing a pulse sequence protocol parameter statistic 366. The pulse sequence protocol parameter statistic 366 contains a statistical description of at least some of the pulse sequence protocols within the pulse sequence database 362.

The computer memory 334 is shown as containing computer executable instructions for execution by the processor 328. The computer memory 334 contains a control module 370. The control module 370 contains computer executable code for controlling the operation and function of the therapeutic apparatus 300. The computer memory 334 is shown as further containing an image reconstruction module 372. The image reconstruction module may contain computer executable code for reconstructing the magnetic resonance data 348 into the magnetic resonance image 350. The computer memory 334 is shown as further containing an image segmentation module 374. The image segmentation module 374 may be implemented using known and standard image segmentation algorithms and techniques. Image segmentation module 374 may be for instance used for generating the set of image segmentations 356. It may also be used for identifying the anatomical structure 322 in the magnetic resonance image 350.

The computer memory 334 further contains a type classification module 376. The type classification module 376 may be used for generating the pulse sequence type classification 342 from the pulse sequence protocol 340. The computer memory 334 is further shown as containing a contrast classification module 378. The contrast classification module 378 may be used for generating the magnetic resonance contrast classification 344 using the pulse sequence type classification 342 and the pulse sequence protocol 340. The computer memory 334 is further shown as containing a protocol classification module 380. The protocol classification module 380 contains computer executable code for creating the pulse sequence protocol classification 346 using the magnetic resonance contrast classification 344, the pulse sequence type classification 342 and/or the pulse sequence protocol 340.

The computer memory 334 further contains a graphical user interface module 382 for controlling the operation and function of a graphical user interface 391. The computer memory 334 is further shown as containing an anatomical structure comparison module 384. The anatomical structure comparison module 384 is adapted for using the image segmentations 356 and generating the comparison 358 of anatomical structures. The computer memory 334 is further shown as containing a data mining module 386. The data mining module 386 contains computer executable code for examining the pulse sequence database 362 and/or the image base 352. The data mining module 386 may be therefore used to generate the pulse sequence protocol parameter statistic 366 and/or the class-specific parameter statistic 360.

Part of the user interface 330 is a display 390. The display 390 is displaying a graphical user interface 391. The graphical user interface 391 has several parameter adjusters 392 for adjusting the various parameters of the pulse sequence protocol 340. The values 393 indicate a current parameter value. The values 394 indicate a desired range which the current parameter values may have. Also displayed on the graphical user interface 391 is a warning message 395. The warning message 395 instructs the operator to modify the flip angle. The numerical range indicated by 396 constitutes a corrective modification. The operator then has the option of adjusting the flip angle using the parameter adjuster 392. When the operator is finished he or she may click on the continue data entry selector 397. When this is clicked modifications 368 to the pulse sequence protocol 340 are generated. The modifications 368 are shown as being stored in the computer storage 332.

Figure 4:
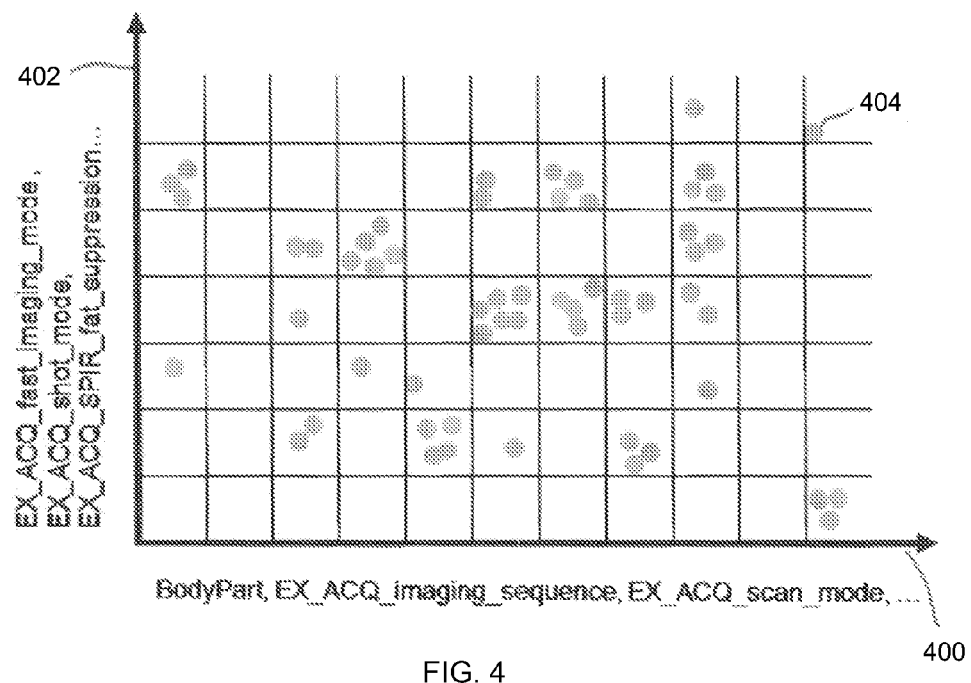
FIG. 4 shows a plot which illustrates the binning of pulse sequence protocols.
Figure 5:
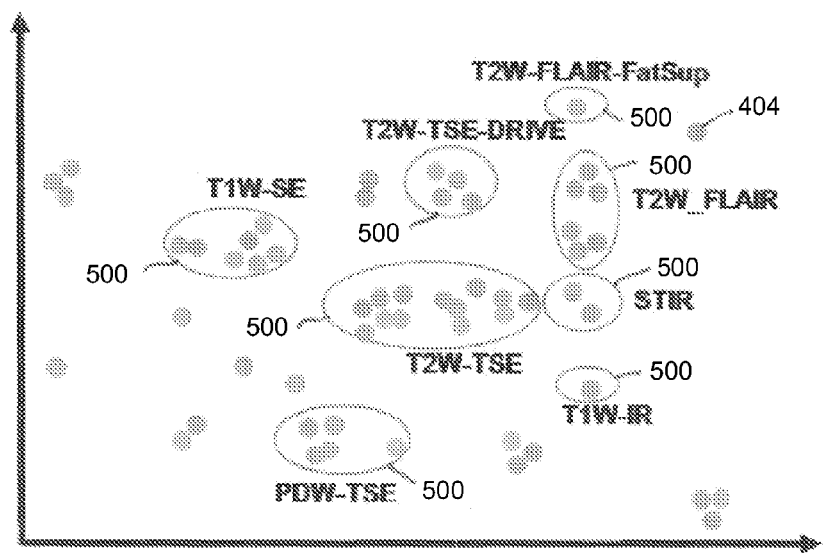
FIG. 5 shows a plot which groups the bins of FIG. 4 into pulse sequence protocol classifications.

FIGS. 4 and 5 illustrate graphically how a method of determining a pulse sequence protocol classification is performed. The graph in 4 is divided into a series of bins. On the x-axis there are bins for the parameters on which the pulse sequence type classification is descriptive of. The y-axis is also divided into a series of bins representative of other parameters on which the pulse sequence type classification is descriptive of. The dots 404 are the pulse sequence protocols. Only one dot 404 is labeled. FIG. 5 shows that the pulse sequence protocols 404 are then divided into groups which are then identified as pulse sequence protocol classifications 500.

Figure 6:
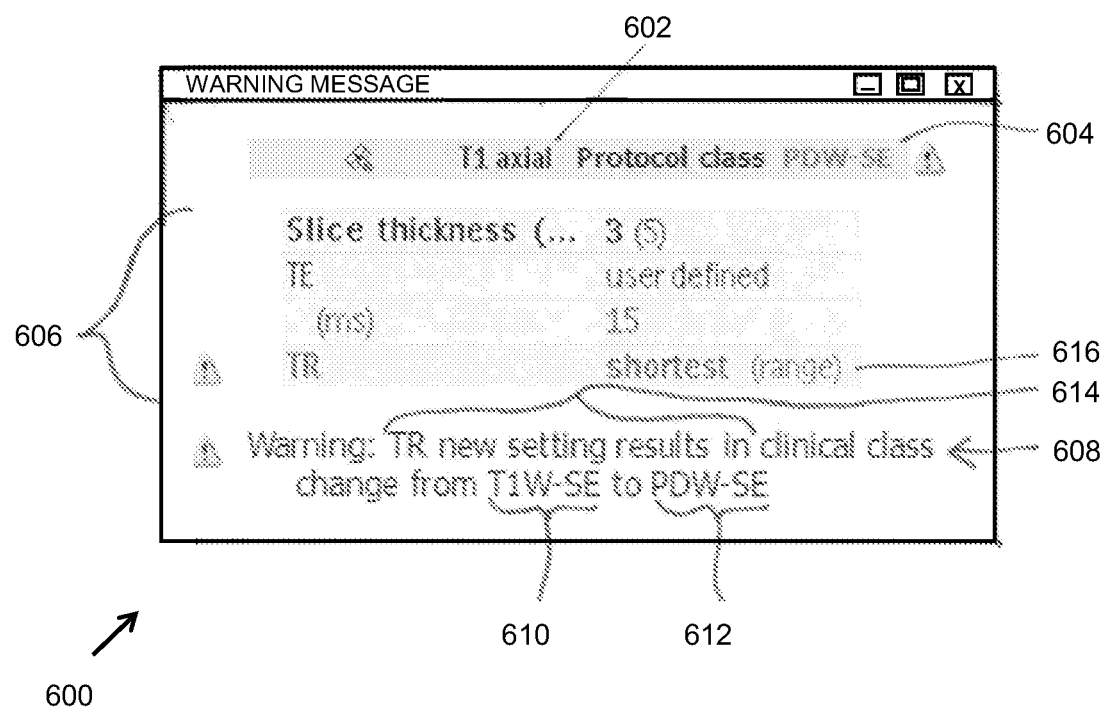
FIG. 6 shows a warning message displayed on a display according to an embodiment of the invention.

FIG. 6 shows a graphical user interface 600 for displaying a warning message 608 according to an embodiment of the invention. Within the graphical user interface the pulse sequence protocol name 602 is displayed. In this case it is a T1 axial scan. Adjacent to the pulse sequence protocol name 602, the current pulse sequence protocol classification 604 is displayed. In this case it is PDW-SE. The list of the pulse sequence parameters 606 is displayed. Below this the warning message 608 is displayed. Within the warning message 608 the initial pulse sequence protocol classification 610 is displayed. In this case it is T1W-SE. Also within the warning message 608 is the current pulse sequence protocol classification 612. This is identical with what was displayed as item 604. Also within the warning message 608 is a correction message 614 indicating that the TR or time repetition setting resulted in the class change from T1W-SE to PDW-SE. Also displayed within the pulse sequence parameters 606 the TR parameter is highlighted and is also a correction message 616. While the invention has been illustrated and described in detail in the drawings and foregoing description, such illustration and description are to be considered illustrative or exemplary and not restrictive; the invention is not limited to the disclosed embodiments.

A graphical user interface may be used as a magnetic resonance protocol editor. It may display the pulse sequence protocol class, e.g., on the info page, and to highlight (using color or bold font) changes in the pulse sequence protocol class 608 due to parameter changes performed by the operator. Alternatively, a confirmation box 600 can be displayed to the operator if the contrast class has been changed from the original one. In a preferred embodiment, this alert or notification is given at the instant that the classification unit compares the current class 612 with the initial class 610 and determines that there is a difference. In an alternative embodiment, this alert or notification is given upon a specified user interaction, such as when the user saves the protocol or asks for the system to check for contrast change.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 300 medical imaging device
302 magnetic resonance imaging system
304 magnet
306 bore of magnet
308 imaging zone
310 magnetic field gradient coils
312 magnetic field gradient coil power supply
314 radio frequency coil
316 transceiver
318 subject
320 subject support
322 anatomical structure
324 computer system
326 hardware interface
328 processor
330 user interface
332 computer storage
334 computer memory
336 selected pulse sequence protocol
338 initial pulse sequence protocol classification
340 pulse sequence protocol
342 pulse sequence type classification
344 magnetic resonance contrast classification
346 pulse sequence protocol classification
348 magnetic resonance data
350 magnetic resonance image
352 image database
354 set of magnetic resonance images
356 image segmentation of set of images
358 comparison of anatomical structure
360 class-specific parameter statistic
362 pulse sequence database
364 pulse sequence protocol classification tag
366 pulse sequence protocol parameter statistic
368 modifications to pulse sequence protocol
370 control module
372 image reconstruction module
374 image segmentation module
376 type classification module
378 contrast classification module
380 protocol classification module
382 graphical user interface module
384 anatomical structure comparison module
386 data mining module
390 display
391 graphical user interface
392 parameter adjuster
393 current parameter value
394 desired range
395 warning message
396 corrective modification
397 data entry selector
400 bins for pulse sequence type classification
402 bins for pulse sequence type classification
404 representative pulse sequence protocol
500 pulse sequence protocol classification
600 graphical user interface
602 pulse sequence protocol name/pulse sequence protocol classification
604 current pulse sequence protocol classification
606 pulse sequence parameters
608 warning message
610 initial pulse sequence protocol classification
612 pulse sequence protocol classification
614 correction message
616 correction message

The invention claimed is:

1. A medical imaging device comprising:
a magnetic resonance imaging system for acquiring magnetic resonance data;
a processor for controlling the medical imaging device;
a memory containing machine executable instructions for execution by the processor, wherein execution of the instructions controls the processor to:
receive an initial pulse sequence protocol, wherein the initial pulse sequence protocol comprises device protocol parameters and instructions which control the magnetic resonance imaging system to acquire the magnetic resonance data;
determine an initial pulse sequence classification of the initial pulse sequence protocol;
receive modifications to the initial pulse sequence protocol;
modify the initial pulse sequence protocol with the received modifications to determine a modified pulse sequence protocol;
determine a modified pulse sequence classification of the modified pulse sequence protocol;
determine a magnetic resonance contrast classification based on the modified pulse sequence classification;
determine a modified pulse sequence protocol classification based on the modified pulse sequence classification and the determined magnetic resonance contrast classification;
determine corrective modifications to the modified pulse sequence protocol when the modified pulse sequence protocol classification is changed from the initial pulse sequence protocol classification to the modified pulse sequence classification, wherein the determined corrective modifications identify further modifications to the modified pulse sequence protocol which will return the modified pulse sequence protocol classification to the initial pulse sequence protocol classification; and
control a display to display a correction message on the display, wherein the correction message is descriptive of the determined corrective modifications.

2. The medical imaging device of claim 1, wherein execution of the instructions further controls the processor to:

display the initial pulse sequence protocol on a graphical user interface such that manipulation of the graphical user interface with a human interface device allows modification of the initial pulse sequence protocol, wherein the modifications are at least partially received from the human interface device;

display allowed modifications on the graphical user interface, wherein the allowed modifications are descriptive of modifications which will return the pulse sequence protocol classification back to the initial pulse sequence protocol classification.

3. The medical imaging device of claim 1, wherein execution of the instructions further controls the processor to:

acquire the magnetic resonance data using the magnetic resonance imaging system in accordance with the pulse sequence protocol; and reconstruct a magnetic resonance image from the magnetic resonance data.

4. The medical imaging device of claim 3, wherein execution of the instruction further controls the processor to control the display to display a warning message when the modified pulse sequence protocol classification is not identical with the initial pulse sequence protocol classification.

5. The medical imaging device of claim 3, wherein execution of the instructions further controls the processor to append a pulse sequence protocol classification tag to the magnetic resonance image.

6. The medical imaging device of claim 5, wherein execution of the instructions further controls the processor to determine a set of magnetic resonance images, wherein the determined set of magnetic resonance images each have an appended pulse sequence protocol tag indicating the pulse sequence protocol.

7. The medical imaging device of claim 6, wherein execution of the instructions further controls the processor to segment the magnetic resonance image and the set of magnetic resonance images.

8. The medical imaging device of claim 7, wherein execution of the instructions further controls the processor to identify an anatomical structure in the segmented magnetic resonance image and the segmented set of magnetic resonance images.

9. The medical imaging device of claim 5, wherein execution of the instructions further controls the processor to:

access an image database containing magnetic resonance images; and calculate a class-specific parameter statistic descriptive of the database, wherein the class is defined by any one of the following: a pulse sequence classification, a magnetic resonance contrast classification, a pulse sequence protocol classification, and combinations thereof, wherein the parameter is an image feature descriptive of the magnetic resonance images.

10. The medical imaging device of claim 3, wherein the pulse sequence classification comprises one or more of the following: scan type, imaging sequence, scan mode, fast imaging mode, shot mode, diffusion mode, dynamic mode, phase contrast mode, parallel imaging mode, and fat suppression.

11. The medical imaging device of claim 3, wherein the magnetic resonance contrast classification comprises one or more of the following: echo time, repetition time, inversion delay, flip angle, diffusion b-value, and voxel size.

12. A method of operating a medical imaging device, wherein the medical image device comprises a magnetic resonance imaging system for acquiring magnetic resonance data, wherein the method comprises:

with one or more processors, retrieving an initial pulse sequence protocol from a memory, wherein the initial pulse sequence protocol comprises device protocol parameters and instructions which control the magnetic resonance imaging system to acquire the magnetic resonance data;

with the one or more processors, determining an initial pulse sequence classification of the initial pulse sequence protocol;

with the one or more processors, determining an initial magnetic resonance contrast classification based on the initial determined pulse sequence classification;

with the one or more processors, determining an initial pulse sequence protocol classification based on the initial pulse sequence classification and the determined initial magnetic resonance contrast classification;

receiving modifications to the initial pulse sequence protocol from a user input device to create a modified pulse sequence protocol, with the one or more processors, determining a modified pulse sequence classification of the modified pulse sequence protocol;

with the one or more processors, determining a modified magnetic resonance contrast classification based on the modified pulse sequence classification;

with the one or more processors, determining a modified pulse sequence protocol classification based on the modified pulse sequence classification and the modified magnetic resonance contrast classification;

with the one or more processors, comparing the initial pulse sequence protocol classification and the modified pulse sequence protocol classification;

with the one or more processors, in response to the modified pulse sequence protocol classification differing from the initial pulse sequence protocol classification, determining modifications to the modified pulse sequence protocol which cause the initial pulse sequence protocol classification and the modified pulse sequence protocol classification to match and controlling a display to display the modifications to the initial pulse sequence protocol;

with the one or more processors, in response to the modified pulse sequence protocol classification matching the initial pulse sequence protocol classification, controlling a magnetic resonance imager to acquire magnetic resonance data; and with the one or more processors, reconstructing the acquired magnetic resonance data into a magnetic resonance image.

13. The method according to claim 12, wherein the magnetic resonance contrast classification comprises one or more of the following: echo time, repetition time, inversion delay, flip angle, diffusion b-value, and voxel size.

14. The method according to claim 13, wherein the pulse sequence classification comprises one or more of the following: scan type, imaging sequence, scan mode, fast imaging mode, shot mode, diffusion mode, dynamic mode, phase contrast mode, parallel imaging mode, and fat suppression.

15. The method according to claim 12, further including, with the one or more processors:

appending a pulse sequence protocol tag to the reconstructed image indicating the pulse sequence protocol that was used to acquire the magnetic resonance data.

16. The method according to claim 12, further including, with the one or more processors:

segmenting the reconstructed magnetic resonance image; and identifying anatomical structures in the segmented magnetic resonance image.

17. The method according to claim 12, further including, with the one or more processors:

calculate a class-specific image feature descriptive of the magnetic resonance image, wherein the class is defined by any one of the following:

a pulse sequence classification, a magnetic resonance contrast classification, a pulse sequence protocol classification, and combinations thereof.

18. A non-transitory computer-readable medium carrying instructions for controlling one or more processors to carry out the method of claim 12.

19. The method according to claim 12, further including, with the one or more processors:

further modifying the modified pulse sequence protocol with the determined corrective modifications before controlling the magnetic resonance imaging device to acquire the magnetic resonance data.

20. A medical imaging system including:

a pulse sequence protocol memory configured to store pulse sequence protocols;

a user input device;

a display device; and one or more processors configured to perform:

retrieving an initial pulse sequence protocol from the pulse sequence protocol memory, wherein the initial pulse sequence protocol comprises device protocol parameters and instructions which control the magnetic resonance imaging system to acquire the magnetic resonance data;

determining an initial pulse sequence classification of the initial pulse sequence protocol;

determining an initial magnetic resonance contrast classification based on the initial determined pulse sequence classification;

determining an initial pulse sequence protocol classification based on the initial pulse sequence classification and the determined initial magnetic resonance contrast classification;

receiving modifications to the initial pulse sequence protocol from the user input device to create a modified pulse sequence protocol, determining a modified pulse sequence classification of the modified pulse sequence protocol;

determining a modified magnetic resonance contrast classification based on the modified pulse sequence classification;

comparing the initial magnetic resonance contrast classification and the modified magnetic resonance contrast classification;

in response to the modified magnetic resonance contrast classification differing from the initial magnetic resonance contrast classification, determining modifications to the modified pulse sequence protocol which cause the initial magnetic resonance contrast classification and the modified magnetic resonance contrast classification to match and controlling the display to display the modifications to the pulse sequence protocol;

in response to the modified magnetic resonance contrast classification matching the initial magnetic resonance contrast classification, controlling a magnetic resonance imager to acquire magnetic resonance data; and reconstructing the acquired magnetic resonance data into a magnetic resonance image.

* * * * *